(12) United States Patent
Bushmaker (10) Patent No.: US 9,766,127 B2
(45) Date of Patent: Sep. 19, 2017

(54) TERAHERTZ DETECTION ASSEMBLY AND METHODS FOR USE IN DETECTING TERAHERTZ RADIATION

(71) Applicant: The Aerospace Corporation, ElSegundo, CA (US)

(72) Inventor: Adam Wayne Bushmaker, Los Angeles, CA (US)

(73) Assignee: The Aerospace Corporation, El Segundo, CA (US)

( * ) Notice: Subject to any disclaimer, the term of this patent is extended or adjusted under 35 U.S.C. 154(b) by 174 days.

(21) Appl. No.: 13/942,656

(22) Filed: Jul. 15, 2013

(65) Prior Publication Data

US 2015/0014535 A1 Jan. 15, 2015

(51) Int. Cl.
G01J 5/20 (2006.01)
G01J 3/42 (2006.01)
G01N 21/3581 (2014.01)
G01R 23/17 (2006.01)

(52) U.S. Cl.
CPC ............ G01J 3/42 (2013.01); G01N 21/3581 (2013.01); G01R 23/17 (2013.01)

(58) Field of Classification Search
CPC ........... G01N 21/6428; G01N 21/6458; G01N 21/64; G01N 21/6408; G01N 2021/6421
See application file for complete search history.

(56) References Cited

U.S. PATENT DOCUMENTS

| | | | |
|---|---|---|---|
| 5,914,497 | A | 6/1999 | Sherwin |
| 7,230,244 | B2 | 6/2007 | Trotz et al. |
| 7,272,158 | B1 | 9/2007 | Hayes et al. |
| 7,326,930 | B2 | 2/2008 | Crawely |
| 7,620,508 | B2 | 11/2009 | Chamberlin et al. |
| 8,330,111 | B2 | 12/2012 | Ojefors et al. |
| 8,373,123 | B2 | 2/2013 | Ouvrier-Buffet |

(Continued)

OTHER PUBLICATIONS

Barrientos, C., et al.; "Vertically illuminated TW-UTC photodiodes for terahertz generation. *In Proc SPIE.*"; 2010.

(Continued)

*Primary Examiner* — David Porta
*Assistant Examiner* — Mamadou Faye
(74) *Attorney, Agent, or Firm* — Manita Rawat; Duane Morris LLP (57) ABSTRACT

A terahertz detection assembly generally has a light generating apparatus configured to generate at least one illuminating light pattern and a substrate member positioned proximate to the light generating apparatus. The substrate member includes a semiconductive portion configured to receive at least a portion of the illuminating light pattern such that a conductive path is defined within the semiconductive portion. At least one waveguide is coupled to the semiconductive portion such that the waveguide is adjacent to the conductive path. The waveguide is configured to receive at least a portion of the illuminating light pattern such that the pattern is moving along the waveguide. The waveguide is further configured to receive a plurality of terahertz electromagnetic waves that are transmitted within the waveguide in the same direction as the motion of the illuminating light pattern to facilitate the detection and characterization of the terahertz electromagnetic waves.

22 Claims, 4 Drawing Sheets

(56) References Cited

U.S. PATENT DOCUMENTS

| | | | |
|---|---|---|---|
| 2005/0156110 A1 | 7/2005 | Crawely | |
| 2006/0049356 A1 | 3/2006 | Davies et al. | |
| 2006/0167641 A1 | 7/2006 | Chamberlin et al. | |
| 2008/0151349 A1* | 6/2008 | Hochberg et al. | 359/258 |
| 2010/0084570 A1* | 4/2010 | Katagiri | 250/458.1 |
| 2010/0102233 A1 | 4/2010 | Gelmond | |
| 2010/0155605 A1* | 6/2010 | Choi | G01J 3/02 250/347 |
| 2010/0184245 A1 | 7/2010 | Dubarry et al. | |
| 2010/0276597 A1 | 11/2010 | Ouvrier-Buffet | |
| 2010/0310976 A1 | 12/2010 | Kajiki | |
| 2011/0127432 A1 | 6/2011 | Federici et al. | |
| 2011/0149368 A1* | 6/2011 | Kim et al. | 359/276 |
| 2011/0267599 A1 | 11/2011 | Hurley | |
| 2012/0049072 A1 | 3/2012 | Itsuji et al. | |
| 2012/0068090 A1* | 3/2012 | Park | 250/493.1 |
| 2012/0097850 A1* | 4/2012 | Darcie | G01J 3/0205 250/340 |
| 2012/0318983 A1 | 12/2012 | Ouchi | |
| 2013/0063159 A1* | 3/2013 | Koyama | G02B 6/1226 324/639 |

OTHER PUBLICATIONS

Chiu, et al.; "*High-Speed Low-Temperature-Grown GaAs p-i-n Traveling-Wave Photodetector*"; IEEE Photonics Technology Letters, vol. 10, No. 7; Jul. 1998; pp. 1012-1014.

Duerr, E.K., K.A. Mcintosh, and S. Verghese; "*Design of a Distributed TeraHertz Photomixer, in Tenth international Symposium on Space Terahertz Technology.*"; 1999: Charlottesville.

Exter Martin van, Fattinger, Ch., and Grischkowsky, D.; "*High brightness terahertz beams characterized with an ultrafast detector*"; Applied Physics Letters. 55, 337; (1989); pp. 337-339.

Gan, Kian-Giap, et al.; "*Ultrahigh power-bandwidth-product performance of low-temperature-grown-GaAs based metal-semiconductor-metal traveling-wave photodetectors*"; Applied. Physics. Letter, vol. 80, No. 21; May 27, 2002; pp. 4054-4056; available online at http://dx.doi.org/10.1063/1.1482139.

Jepsen, P.U., R.H. Jacobsen, and S.R. Keiding; "*Generation and detection of terahertz pulses from biased semiconductor antennas.*"; J. Opt. Soc. Am. B, 1996. 13(11); pp. 2424-2436.

Lasaosa, Daniel, et al; "*Traveling-Wave Photodetectors With. High Power-Bandwidth and Gain-Bandwidth Product Performance*"; IEEE Journal of Selected Topics in Quantum Electronics, vol. 10, No. 4; Jul./Aug. 2004; pp. 728-741.

Matsuura, S., et al.; "*A traveling-wave THz photomixer based on angle-tuned phase matching.*"; Applied Physics Letters, 1999. 74(19): p. 2872-2874.

Michael, E. A., et al.; "*Large-area traveling-wave photonic mixers for increased continuous terahertz power*"; Applied. Physics. Letter 86, (2005); pp. 111120-1-111120-3; available online at http://dx.doi.org/10.1063/1.1884262.

Michael, E. A., et al.; "*Terahertz continuous-wave large-area traveling-wave photomixers on highenergy low-dose ion-implanted GaAs*"; Applied. Physics. Letter 90; (2007); pp. 171109-1-171109-3; available online at http://dx.doi.org/10.1063/1.2722235.

Page, H., et al.; "*Waveguide coupled terahertz photoconductive antennas: Toward integrated photonic terahertz devices.*"; Applied Physics Letters, 2008. 92: pp. 163502-1-163502-3.

Taylor, H. F., et al; "*Traveling Wave Photodetectors*"; Optoelectronic Signal Processing for Phased-Array Antennas II; (1990); pp. 59-63.

Shi, Jin-Wei, et al.; "*Ultrahigh-Power-Bandwidth Product and Nonlinear Photoconductance Performances of Low-Temperature-Grown GaAs-Based Metal-Semiconductor—Metal Traveling-Wave Photodetectors*";IEEE Photonics Technology Letters, vol. 14, No. 11; Nov. 2002; pp. 1587-1589.

Verghese, S., et al., "*Generation and detection of coherent terahertz waves using two photomixers.*"; Applied Physics Letters,.73(26): (1998); pp. 3824-3826.

Weling, A., et al.; "*Generation of tunable narrow-band THz radiation from large aperture photoconducting antennas*";. Applied Physics Letters, 64(2); (1994); pp. 137-139; available online at http://dx.doi.org/10.1063/1.111543.

Yin, X., B.W.-H. NG, and D. Abbott; "*Terahertz Imaging for Biomedical Applications; Pattern Recognition and Tomographic Reconstruction, Chapter 2: THz sources and detectors.*"; 2012: Springer.

* cited by examiner

TERAHERTZ DETECTION ASSEMBLY AND METHODS FOR USE IN DETECTING TERAHERTZ RADIATION

BACKGROUND

The invention relates generally to detection and useful application of electromagnetic waves and, more particularly, to a terahertz detection assembly. The invention can be used in systems and methods for detecting terahertz radiation that has been applied to a sample or subject in connection with determining characteristics of the sample or subject.

Terahertz radiation or terahertz waves include electromagnetic waves at frequencies in the range of about 0.3 terahertz to about 3.0 terahertz. There are applications for terahertz radiation in the civil, defense, and commercial markets. For example, the capability of terahertz radiation to penetrate into certain materials or media such as fabrics and plastics makes this wavelength useful in surveillance technologies and in methods for detecting or imaging the characteristics of a sample or subject. (Hereinafter, any medium to which such radiation is applied will be termed the "sample.") Terahertz radiation may also be used for the evaluation of materials, rockets, and satellite structural components.

When using terahertz radiation to evaluate materials, terahertz radiation is generated and is channeled to an emitter such that terahertz waves are propagated onto the sample being evaluated. The extent to which terahertz waves are absorbed by the sample can be ascertained by detecting the terahertz waves that move adjacent to the sample or are transmitted through some thickness of the sample material and by comparing a quantity of the detected waves with the overall terahertz radiation that was directed to the sample. A determination of the terahertz waves that are absorbed by the sample can facilitate ascertaining various characteristics of the sample. Variations in absorption, reflection and/or transmission can be resolved locally to produce images.

There are various techniques that can be used to detect the terahertz radiation after being directed at the sample. For example, terahertz radiation can be detected by sensitive bolometric methods. Coherent techniques can also be used to detect terahertz signals from sources with a known phase, such as sources wherein terahertz signals are generated using pulsed or photomixed lasers. Electro-optic sampling can also be used. This technique uses nonlinear optical crystals, along with photoconductive switching. While such techniques facilitate the detection of terahertz radiation, such techniques are not very sensitive. As a result, several sources and/or detectors for terahertz waves are needed to perform the analysis. Accordingly, known detection techniques using terahertz radiation are not efficient.

BRIEF DESCRIPTION

In one embodiment, a terahertz detection assembly is provided. The terahertz detection assembly includes a light generating apparatus configured to generate at least one illuminating light pattern and a substrate member positioned proximate to the light generating apparatus. The substrate member includes a semiconductive portion configured to receive at least a portion of the illuminating light pattern such that a conductive path is defined within the semiconductive portion. At least one terahertz waveguide is coupled to the semiconductive portion such that the terahertz waveguide is adjacent to the conductive path. The terahertz waveguide is configured to receive at least a portion of the illuminating light pattern such that the pattern is moving along the waveguide. The waveguide is further configured to receive a plurality of terahertz electromagnetic waves that are transmitted within the waveguide in the same direction as the illuminating light pattern from the light generating apparatus to facilitate the detection and characterization of the terahertz electromagnetic waves.

In another embodiment, a method of detecting terahertz radiation is provided. The method includes positioning a substrate member proximate to a light generating apparatus, wherein the substrate member includes a semiconductive portion and at least one waveguide that is coupled to the semiconductive portion. At least one illuminating light pattern is generated by the light generating apparatus. At least a portion of the illuminating light pattern is directed onto the semiconductive portion such that a conductive path is defined therein. At least a portion of the illuminating light pattern is received via the waveguide such that the light pattern is moving along the waveguide. A plurality of terahertz electromagnetic waves are received via the waveguide such that the terahertz electromagnetic waves are transmitted within the waveguide in the same direction as the illuminating light pattern from light generating device to facilitate the detection and characterization of the terahertz electromagnetic waves.

In yet another embodiment, a system is provided. The system includes an antenna and a terahertz detection assembly that is coupled to the antenna. The terahertz detection assembly includes a light generating apparatus configured to generate at least one illuminating light pattern and a substrate member positioned proximate to the light generating apparatus. The substrate member includes a semiconductive portion configured to receive at least a portion of the illuminating light pattern such that a conductive path is defined within the semiconductive portion. At least one waveguide is coupled to the semiconductive portion such that the waveguide is adjacent to the conductive path. The waveguide is configured to receive at least a portion of the illuminating light pattern such that the light pattern is moving along the waveguide. The waveguide is further configured to receive a plurality of terahertz electromagnetic waves that are transmitted within the waveguide in the same direction as the illuminating pattern from the light generating apparatus to facilitate the detection and characterization of the terahertz electromagnetic waves.

DETAILED DESCRIPTION

The exemplary assemblies, systems, and methods described herein provide an efficient solution to detecting terahertz radiation. More specifically, the embodiments described herein provide a light generating apparatus that is configured to generate at least one illuminating light pattern that can be directed onto a substrate member having at least one waveguide and a semiconductive portion. As the illuminating light pattern is directed onto the substrate, the waveguide also receives a plurality of terahertz electromagnetic waves. The waves can be transmitted within the waveguide in the same direction as the motion of the illuminating light pattern from the light generating apparatus. Such a technique facilitates the generation of a current that can be detected and further analyzed to facilitate the characterization of the terahertz electromagnetic waves that were received by the waveguide. The terahertz electromagnetic waves received by the waveguide can be waves that have interacted with a sample, such as by being transmitted through the sample or passed adjacent to the sample. The detection technique is relatively sensitive in detecting terahertz radiation. As such, a relatively large intensity wave source is not needed in, for example, evaluating the sample.

Figure 1:
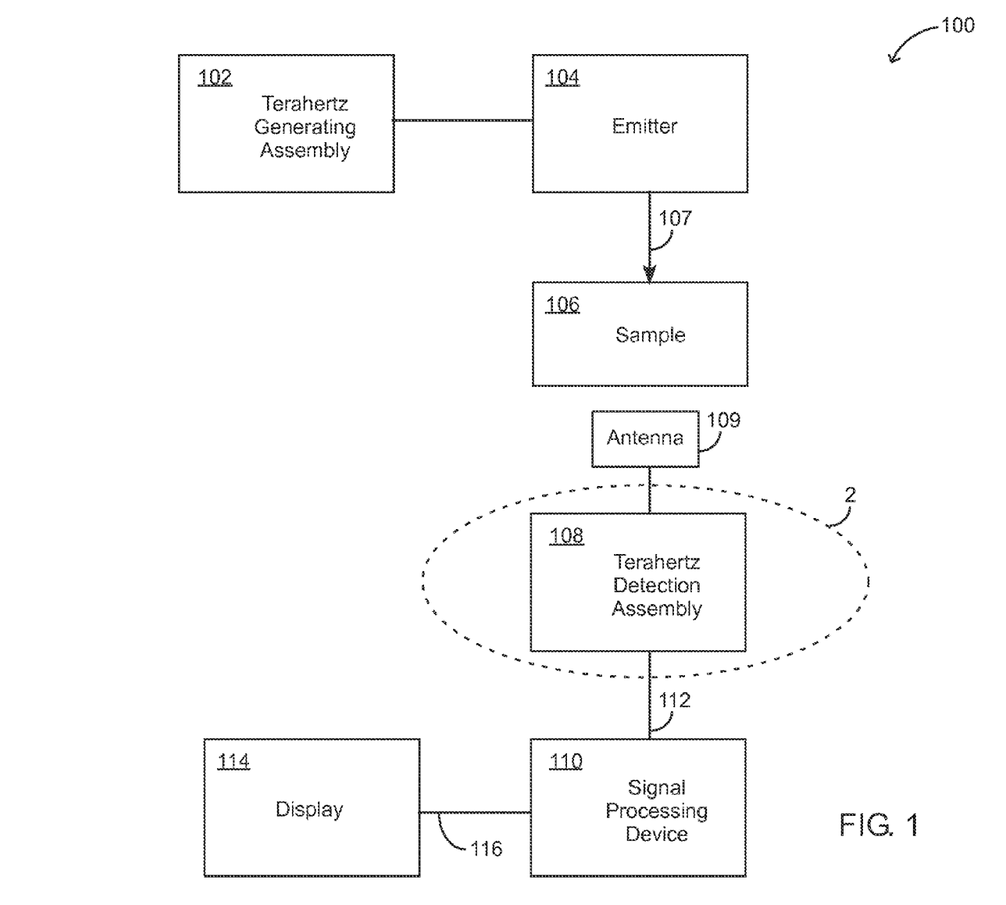
FIG. 1 is block diagram of an exemplary system.

FIG. 1 illustrates an exemplary system 100. In the exemplary embodiment, system 100 is a spectroscopy system that is configured to facilitate the characterization of a component or a chemical reaction as the sample. Although the exemplary embodiment illustrates a spectroscopy system, the present disclosure is not limited to spectroscopy systems and one of ordinary skill in the art will appreciate that the current disclosure may be used in connection with any type of system, such as, for example, a satellite communication system.

System 100 includes a terahertz generating assembly 102 that is coupled to an emitter 104. In the exemplary embodiment, terahertz generating assembly 102 is configured to generate terahertz radiation (i.e., electromagnetic waves at frequencies in the range of about 0.3 terahertz to about 3.0 terahertz and sometimes described as submillimeter wavelengths). For example, terahertz generating assembly 102 can comprise the terahertz generating assembly described in co-pending U.S. patent application Ser. No. 13/728,688 entitled SYSTEMS AND METHODS FOR USE IN GENERATING PULSED TERAHERTZ RADIATION filed Jan. 23, 2013. Moreover, while only one emitter 104 is illustrated in FIG. 1, system 100 may include a plurality of emitters 104 that are each coupled to assembly 102 at various locations. It should be noted that, as used herein, the term "couple" is not limited to a direct mechanical and/or an electrical connection between components, but may also include an indirect mechanical and/or electrical connection between two or more components or a coupling that is operative through intermediate elements or spaces.

In the exemplary embodiment, a sample 106 that is being tested or evaluated, such as a satellite structural component or material, is positioned proximate to emitter 104 such that terahertz electromagnetic waves may be propagated from emitter 104 to sample 106, as shown by arrow 107. An antenna 109 (shown generally) is positioned proximate to sample 106 and configured to receive the terahertz electromagnetic waves in a manner that permits variations to be detected with respect to terahertz wave energy that has been more or less passed adjacent to sample 106 and/or perhaps transmitted through a thickness of the sample 106. That is, the antenna receives terahertz electromagnetic waves that have been affected by sample 106 after being directed at the sample. A terahertz detection assembly 108 is coupled to antenna 109. As explained in more detail below with respect to FIGS. 2 and 3, terahertz detection assembly 108 is configured to detect the terahertz electromagnetic waves that are received by antenna 109 (i.e., the terahertz electromagnetic waves that have not been absorbed by sample 106). The detection can include responding to an amplitude of received/detected terahertz radiation that exceeds a minimum threshold, or responding to variations in received amplitude, etc.

A signal processing device 110 is coupled to terahertz detection assembly 108 via a data conduit 112. Alternatively, signal processing device 110 may be wirelessly coupled to terahertz detection assembly 108 through one or more transceivers (not shown). In the exemplary embodiment, signal processing device 110 is configured to receive at least one signal that is representative of the detected terahertz radiation from terahertz detection assembly 108. Signal processing device 110 is configured to process and/or analyze the signal(s) received from terahertz detection assembly 108. As used herein, the term "process" refers to performing an operation on, adjusting, filtering, buffering, and/or altering at least one characteristic of a signal. For example, in the exemplary embodiment, signal processing device 110 is a computing device that includes a circuit (not shown) or a processor (not shown) such that signal processing device 110 is configured to utilize digital signal processing techniques to generate an output that is representative of the signal(s) received from terahertz detection assembly 108. Alternatively, signal processing device 110 may be configured to utilize either analog or digital signal processing techniques as well as using a hybrid mix of analog and digital to generate an output that is representative of the signal(s) received from terahertz detection assembly 108. The received signal can be detected for a point on the sample 106, or integrated over an area of the sample as an average, or detected separately for spaced points that are regarded as pixels in a spatially distributed detection technique, such as imaging.

A display device 114 is coupled to signal processing device 110 via a data conduit 116. In the exemplary embodiment, display device 114 is configured to display the output(s) generated by signal processing device 110 to a user. For example, display device 114 may be a visual display device, such as a cathode ray tube (CRT), a liquid crystal display (LCD), an light emitting diode (LED) display, an organic LED display, and/or an "electronic ink" display. Alternatively, display device 114 may be an audio output device that includes an audio adapter and/or a speaker.

During operation, terahertz generating assembly 102 first generates terahertz radiation. For example, in some embodiments, assembly 102 enables a temporal and spatial dispersion of a pulsed light beam, wherein the dispersions are focused to produce at least one moving spot of light to generate pulsed terahertz radiation. The pulsed terahertz radiation is channeled to emitter 104 such that the terahertz electromagnetic waves can be propagated onto sample 106. Also, some waves can be absorbed by sample 106. Antenna 109 receives the terahertz electromagnetic waves that pass adjacent to sample and/or are transmitted through sample 106. Antenna 109 transmits the waves to terahertz detection assembly 108.

As explained in more detail below with respect to FIGS. 2 and 3, terahertz detection assembly 108 detects variations in the extent to which the terahertz electromagnetic waves have transmitted through sample 106 and/or terahertz detection assembly 108 detects the terahertz electromagnetic waves that pass next to sample 106. Terahertz detection assembly 108 transmits at least one signal representative of the detected terahertz radiation to signal processing device 110 via conduit 112. Signal processing device 110 analyzes the signal(s) and an output is generated that can be displayed to a user via display device 114. As such, the user is enabled to characterize sample 106. For example, by using the output representative of the detected terahertz waves (i.e., waves that move adjacent to sample 106 or are transmitted through some thickness of the sample material), the user can compare the detected waves with the overall terahertz radiation that was directed to sample 106. As such, the amount absorbed by sample 106 can be determined, which can facilitate ascertaining various characteristics of sample 106.

Figure 2:
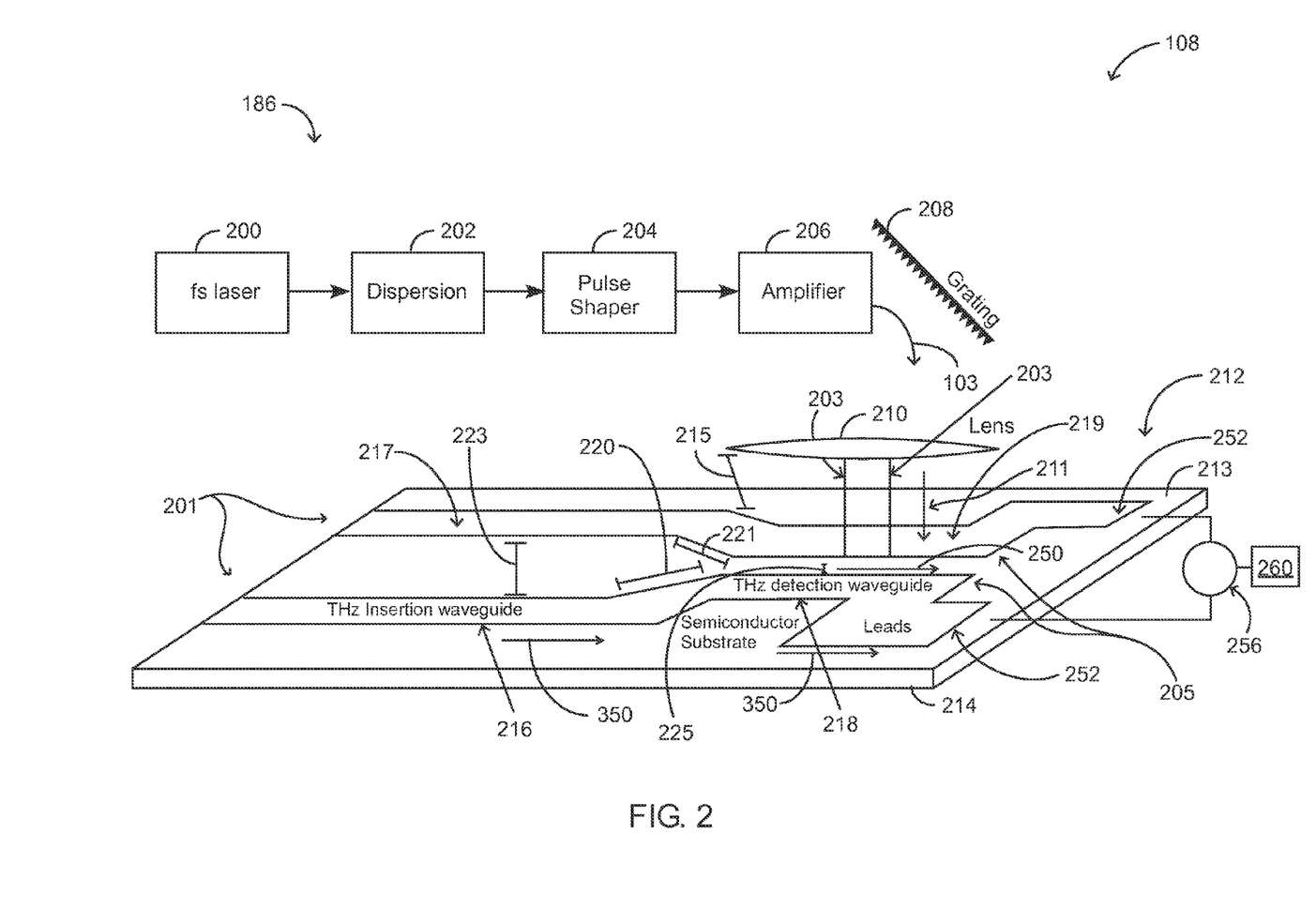
FIG. 2 is a block diagram of an exemplary terahertz detection assembly having a light generating apparatus and a substrate member that may be used with the system shown in FIG. 1 and taken from area 2.

FIG. 2 is a block diagram of terahertz detection assembly 108 taken from area 2 (shown in FIG. 1). In the exemplary embodiment, assembly 108 includes a light generating apparatus 186 that is configured to generate at least one illuminating light pattern, wherein the light pattern can be generated from at least one pulsed light beam. For example, light generating apparatus 186 includes a light emitting device 200 that is configured to generate at least one pulsed light beam that is channeled through assembly 108. Light emitting device 200, in the exemplary embodiment, is a pulsed laser, such as a femtosecond (fs) ultrashort pulsed laser. Alternatively, light emitting device 200 may be any suitable type of laser device or system that enables terahertz detection assembly 108 and/or system 100 (shown in FIG. 1) to function as described herein.

A first dispersion member 202 is positioned proximate to light emitting device 200 such that first dispersion member 202 is enabled to receive pulsed light beams from light emitting device 200. Moreover, first dispersion member 202 is configured to facilitate a temporal dispersion of the pulsed light beam(s) received from light emitting device 200. In the exemplary embodiment, first dispersion member 202 may be a dielectric medium, such as glass or optical fiber. For example, first dispersion member 202 may be a coil of optical fiber. Alternatively, first dispersion member 202 may be any type of medium or component that facilitates a temporal dispersion of light and that enables assembly 108 and/or system 100 to function as described herein.

Assembly 108 may also include a pulse shaper 204 that is positioned proximate to first dispersion member 202 such that pulse shaper 204 may receive the dispersed light beam(s) from first dispersion member 202. In the exemplary embodiment, pulse shaper 204 may be any suitable type of pulse shaper known in the art and includes at least one pulse shaping filter (not shown), such as a trivial boxcar filter, a sinc-shaped filter, a raised-cosine filter, and/or a Gaussian filter.

Pulse shaper 204, in the exemplary embodiment, is configured to tune the dispersion generated by first dispersion member 202. More specifically, pulse shaper 204 is configured to control a pulse shape of the dispersed pulsed light beam(s). Pulse shaper 204 may also be configured to change the delay and the attenuation of the wavelength(s) of the dispersed pulsed light beam(s) received from first dispersion member 202. More specifically, the pulses may be customized for specific performance attributes in various pulsed terahertz applications to add contrast for specific compositions that are present in sample 106 (shown in FIG. 1). Computer optimization algorithms may be used and programmed into, for example, a control system (not shown) that includes a controller (not shown) coupled to pulse shaper 204. Based on the input provided to the control system, the controller may control pulse shaper 204 to optimize various parameters, such as increasing sensitivity to a particular signal of interest (such as a molecular resonance) while decreasing sensitivity to a background signal (such as contributions from a substrate), or bandwidth/sensitivity tradeoff.

Light generating apparatus 186, in the exemplary embodiment, also includes an amplifier 206 that is positioned proximate to pulse shaper 204. Amplifier 206 is configured to amplify the pulsed light beam(s). In the exemplary embodiment, amplifier 206 may be any type of optical amplifier 206 known in the art, such as a doped-fiber amplifier, bulk laser, or a Raman amplifier. Moreover, light generating apparatus 186 includes a second dispersion member 208 that is adjacent to amplifier 206 and positioned proximate to first dispersion member 202 and light emitting device 200. In the exemplary embodiment, second dispersion member 208 may be a prism or a grating that is configured to facilitate a spatial dispersion of the pulsed light beam(s). A lens 210 is positioned adjacent to second dispersion member 208 and proximate to first dispersion member 202, wherein lens 210 is configured to focus the temporal and spatial dispersions of the pulsed light beam(s) to produce at least one moving spot of light 203. Terahertz detection assembly 108 also includes a substrate member 212 that is positioned proximate to lens 210, and moving spot of light 203 is directed onto substrate member 212, as shown by arrows 211.

Instead of using a moving spot of light 203, terahertz detection assembly 108 may use a wave train. For example, referring to FIG. 3, in some embodiments, an alternative light generating apparatus 300 may be used with terahertz detection assembly 108 in place of light generating apparatus 186. Light generating apparatus 300 includes at least two light emitting devices, such as lasers 302 and 304, wherein laser 302 operates at a different wavelength from laser 304. For example, laser 302 operates at $\lambda_1$ and laser 304 operates at $\lambda_2$.

In the exemplary embodiment, a dispersion member 308 is positioned proximate to lasers 302 and 304, wherein dispersion member 308 may be a prism or a grating that is configured to direct the two different wavelength ($\lambda_1$ and $\lambda_2$) light beams received from lasers 302 and 304 onto substrate member 212 at different angles ($\phi_1$ and $\phi_2$, respectively). A mirror 309 is positioned proximate to dispersion member 308 and laser 302 such that mirror 309 is configured to receive the light beams from laser 302. A mirror 311 is positioned proximate to dispersion member 308 and laser 304 such that mirror 311 is configured to receive the light beams from laser 304. Mirror 309 is spaced a predefined distance 315 from mirror 311. The angles ($\phi_1$ and $\phi_2$) are determined by dispersion member 308 and/or the respective mirrors 309 and 311. A lens 310 is positioned adjacent to dispersion member 308 and/or the mirrors 309 and 311, wherein lens 310 is configured to focus the laser beams to produce a moving wave train 312 of a plurality of propagating light beams that are directed onto substrate member 212, as shown by arrows 314. The moving wave train 312 is formed by interference of the two different wavelengths $\lambda_1$ and $\lambda_2$ at substrate member 212.

In some embodiments, one laser can be used as opposed to two different lasers 302 and 304. For example, referring to FIG. 4, an alternative light generating apparatus 400 may be used with terahertz detection assembly 108 in place of light generating apparatus 186 or in place of light generating apparatus 300. Light generating apparatus 400 includes one laser 402 that operates at two different wavelengths ($\lambda_3$ and $\lambda_4$), wherein $\lambda_3$ can be equal to $\lambda_1$ and $\lambda_4$ can be equal to $\lambda_2$.

Figure 4:
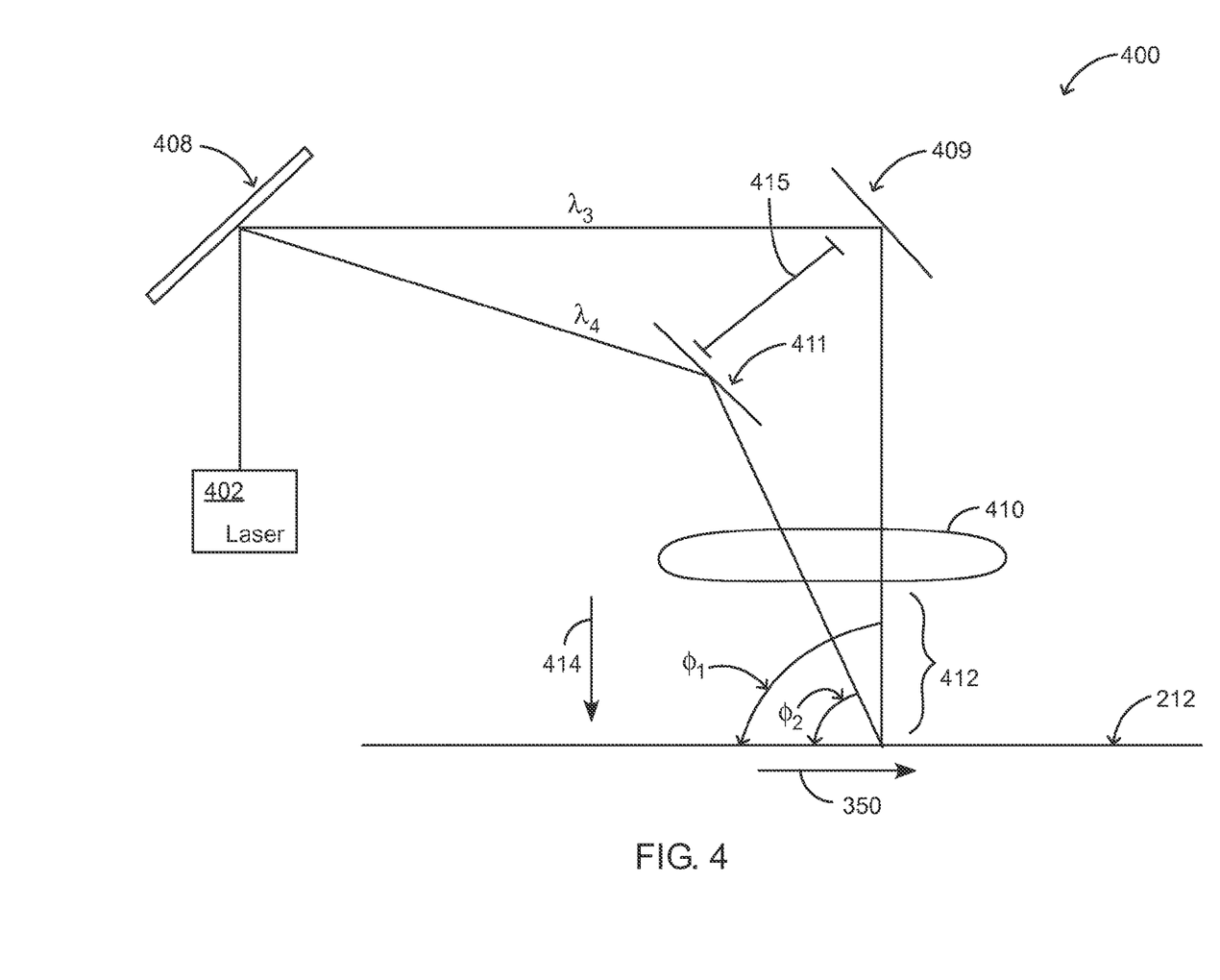
FIG. 4 is a block diagram of an another alternative light generating apparatus that may be used with the terahertz detection assembly shown in FIG. 2.

In the exemplary embodiment, a dispersion member 408 is positioned proximate to laser 402, wherein dispersion member 408 may be a prism or a grating that is configured to direct the two different wavelength ($\lambda_3$ and $\lambda_4$) light beams received from laser 402 onto substrate member 212 at different angles ($\phi_3$ and $\phi_4$, respectively), wherein $\phi_3$ can be equal to $\phi_1$ and $\phi_4$ can be equal to $\phi_2$. A mirror 409 is positioned proximate to dispersion member 408 and laser 402 such that mirror 409 is configured to receive the light beams with wavelength $\lambda_3$ from laser 402. Similarly, a mirror 411 is positioned proximate to dispersion member 408 and laser 402 such that mirror 411 is configured to receive the light beams with wavelength $\lambda_4$ from laser 402. Mirror 409 is positioned a predefined distance 415 from mirror 411. The angles ($\phi_3$ and $\phi_4$) are determined by dispersion member 408 and/or the respective mirrors 409 and 411. A lens 410 is positioned adjacent to dispersion member 408 and/or the mirrors 409 and 411, wherein lens 410 is configured to focus the laser beams to produce a moving wave train 412 of a plurality of propagating light beams that are directed onto substrate member 212, as shown by arrows 414. The moving wave train 412 is formed by interference of the two different wavelengths $\lambda_3$ and $\lambda_4$ at substrate member 212.

Accordingly, the moving spot of light 203 (shown in FIG. 2) generated by light generating apparatus 186 (shown in FIG. 2), the light wave train 312 (shown in FIG. 3) generated by light generating apparatus 300 (shown in FIG. 3), or the light wave train 412 generated by light generating apparatus 400 is directed onto substrate member 212. Referring to FIG. 2, substrate member 212 is a substantially rectangular plate that is fabricated from a semiconducting material, such as Gallium Arsenide. While substrate member 212 is substantially rectangular, substrate member 212 may have any suitable shape that enables assembly 108 and/or system 100 to function as described herein. In the exemplary embodiment, substrate member 212 has a first surface 213 and a second surface 214 fabricated from the semiconducting material, wherein lens 210 is positioned a predefined distance 215 from first surface 213. As such, substrate member first surface 213 being fabricated from the semiconducting material is configured to receive at least a portion of the light pattern or a signal from the light pattern such that a temporary conductive path 250 is defined therein.

In the exemplary embodiment, at least one waveguide, such as terahertz insertion waveguide 201 comprised of conductors 216 and 217 and terahertz detection waveguide 205 comprised of conductors 218 and 219, are coupled to substrate member first surface 213 such that a junction portion 220 is defined between conductor 216 and conductor 218 and a junction portion 221 is defined between conductor 217 and conductor 219. Moreover, conductor 216 is positioned a predefined distance 223 from conductor 217 such that each conductor 216 and 217 is adjacent to semiconductive portion of substrate member first surface 213. Similarly, conductor 218 is positioned a predefined distance 225 from conductor 219 such that each conductor 218 and 219 is adjacent to semiconductive portion of substrate member first surface 213. Subsequently, conductors 218 and 219 are adjacent to temporary conductive path 250 that is defined when the light pattern is directed onto and is in contact with the semiconductive portion of substrate member first surface 213.

In the exemplary embodiment, terahertz detection waveguide comprised of conductors 218 and 219 are positioned proximate to lens 210, and terahertz insertion waveguide comprised of conductors 216 and 217 are configured to receive a plurality of terahertz electromagnetic waves (not shown). The terahertz electromagnetic waves that are received within waveguide 201 comprised of conductors 216 and 217 can then be channeled to waveguide 205 comprised of conductors 218 and 219, respectively, such that the waves can be channeled across substrate member first surface 213. For example, terahertz detection waveguide comprised of conductors 218 and 219 is configured to provide a channel or terminal for the terahertz electromagnetic waves.

At least one connecting device or a lead 252 is coupled to terahertz detection waveguide conductors 218 and 219, wherein each lead 252 is configured to provide an electrical connection between terahertz detection waveguide conductor 218 and an amplifier 256 and an electrical connection between terahertz detection waveguide conductor 219 and amplifier 256. In the exemplary embodiment, amplifier 256 may be any suitable type of amplifier known in the art. In a preferred embodiment, the amplifier 256 is a current amplifier. In the exemplary embodiment, an analog-to-digital converter 260 can be coupled to amplifier 256 to convert the signals received from amplifier 256 and the converted signals can then be transmitted from converter 260 to signal processing device 110 (shown in FIG. 1) via data conduit 112 (shown in FIG. 1).

During operation, terahertz generating assembly 102 (shown in FIG. 1) first generates terahertz radiation that is transmitted to emitter 104 (shown in FIG. 1) such that the terahertz electromagnetic waves can be propagated onto sample 106 and some waves can be absorbed by sample 106. Antenna 109 receives the terahertz electromagnetic waves that pass adjacent to sample and/or are transmitted through sample 106. The waves received by antenna 109 are transmitted to terahertz detection assembly 108 such that the waves received by antenna 109 can be detected and further analyzed.

For example, as shown in FIG. 2, light generating apparatus 186 is activated and light emitting device 200 generates at least one pulsed light beam that is channeled through first dispersion member 202, wherein the pulsed light beam(s) are temporally dispersed. The pulsed light beam(s) are then passed through pulse shaper 204 and amplifier 206. The pulsed light beam(s) are channeled through second dispersion member 208 such that the light beam(s) are spatially dispersed. More specifically, the different wavelengths present are deviated by second dispersion member 208 to different angles. Lens 210 focuses the different wavelengths to at least one moving spot of light 203 onto substrate member 212. Because of the chirp in the pulse introduced by the temporal dispersion element 202, the different wavelengths in the pulse arrive at substrate member 212 at different times, resulting in the moving spot of light 203. The temporal dispersion combined with the spatial dispersion of the grating 208 gives rise to a moving spot of light that moves in the terahertz detection waveguide conductors 218 and 219. Further, pulse shaper 204, in the exemplary embodiment, tunes the dispersion generated by first dispersion member 202 such that the horizontal velocity of the moving spot of light is equal to the terahertz phase velocity in the terahertz detection waveguide conductors 218 and 219.

Figure 3:
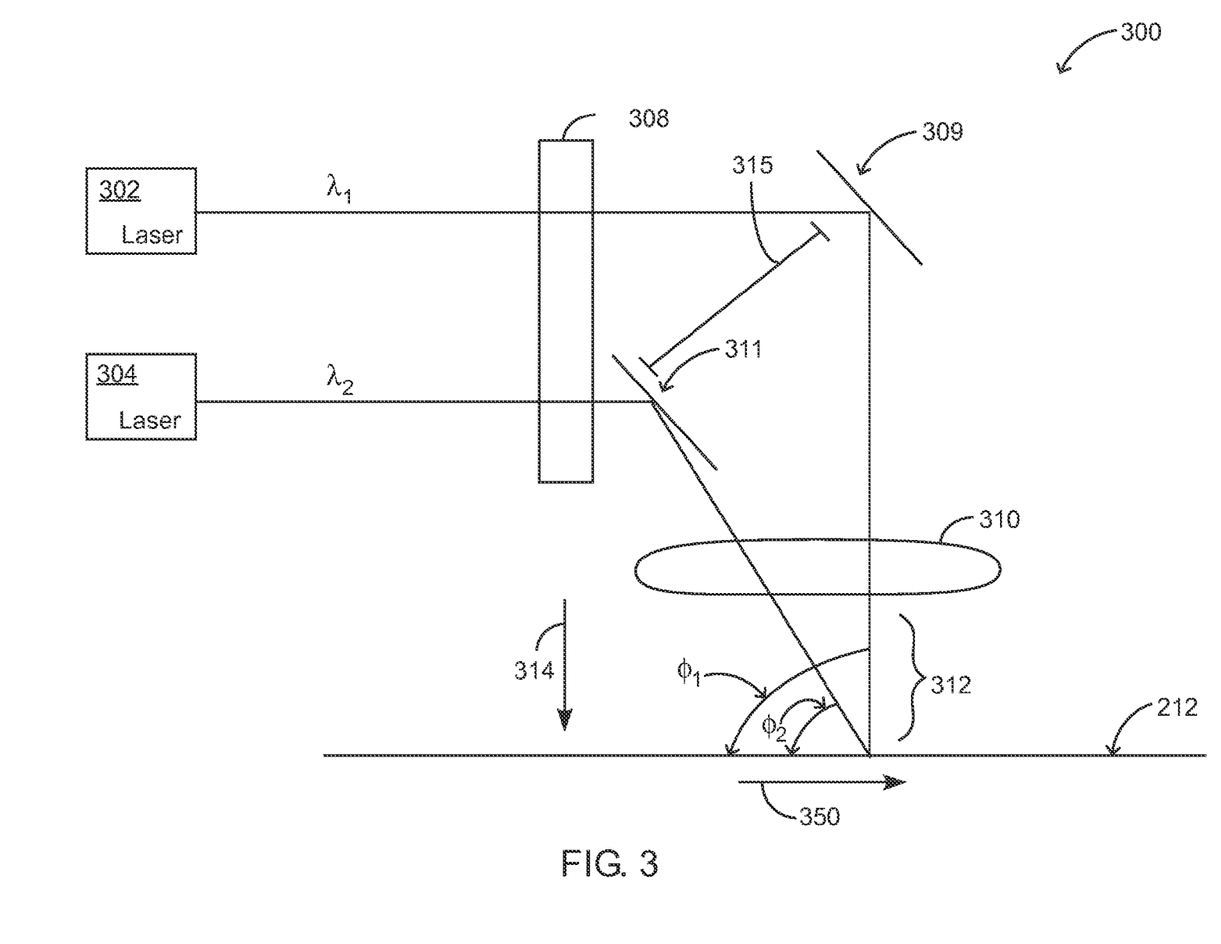
FIG. 3 is a block diagram of an alternative light generating apparatus that may be used with the terahertz detection assembly shown in FIG. 2.

Alternatively, if light generating apparatus 300 (shown in FIG. 3) is used in place of light generating apparatus 186, then lasers 302 (shown in FIG. 3) and 304 (shown in FIG. 3) each generate two separate light beams at two different wavelengths ($\lambda_1$ and $\lambda_2$) (shown in FIG. 3). The light beams are directed onto substrate member 212 at different angles either through positioning of lasers 302 and 304 or through reflections off mirrors 309 (shown in FIG. 3) and 311 (shown in FIG. 3) or other beam steering elements (not shown). Lens 310 (shown in FIG. 3) focuses the light beams to produce a moving wave train 312 of a plurality of propagating light beams that are directed onto substrate member 212. Moving wave train 312 (shown in FIG. 3) is formed by interference of the two different wavelengths ($\lambda_1$ and $\lambda_2$) at substrate member 212. The angles ($\lambda_1$ and $\lambda_2$) (shown in FIG. 3) of the two different wavelength laser beams being generated by lasers 302 and 304, respectively, are tuned such that the group velocity of the wave train 312 matches the phase velocity of the terahertz signal in the terahertz detection waveguide conductors 218 and 219. The angles ($\lambda_1$ and $\lambda_2$) of the two different wavelength laser beams are also tuned so that the wave train envelope frequency is the terahertz detection frequency range.

Instead of using light generating apparatus 300, if light generating apparatus 400 (shown in FIG. 4) is used in place of light generating apparatus 186, then laser 402 (shown in FIG. 4) generates two separate light beams at two different wavelengths ($\lambda_3$ and $\lambda_4$) (shown in FIG. 4). The light beams are directed onto substrate member 212 at different angles either through positioning of laser 402 or through reflections off mirrors 409 (shown in FIG. 4) and 411 (shown in FIG. 4) or other beam steering elements (not shown). Lens 410 (shown in FIG. 4) focuses the light beams to produce a moving wave train 412 of a plurality of propagating light beams that are directed onto substrate member 212. Moving wave train 412 (shown in FIG. 3) is formed by interference of the two different wavelengths ($\lambda_3$ and $\lambda_4$) at substrate member 212. The angles ($\lambda_3$ and $\lambda_4$) (shown in FIG. 4) of the two different wavelength laser beams being generated by laser 402, respectively, are tuned such that the group velocity of the wave train 412 matches the phase velocity of the terahertz signal in the terahertz detection waveguide conductors 218 and 219. The angles ($\lambda_3$ and $\lambda_4$) of the two different laser beams are also tuned such that the wave train envelope frequency is the terahertz detection frequency range.

Accordingly, the moving spot of light generated by light generating apparatus 186, the light wave train 312 generated by light generating apparatus 300, or the light wave train 412 generated by light generating apparatus 400 are directed onto substrate member 212. When any of those illuminating light patterns are directed onto substrate member 212, at least a portion of the light pattern is directed onto the semiconductive material of substrate member first surface 213. As such, the semiconductive material of substrate member first surface 213 is ionized such that temporary conductive pathway 250 is defined between conductor 218 and conductor 219. At least a portion of the light pattern may also be directed onto conductors 218 and 219 such that at least a portion of the illuminating light pattern can be moved, swept, or channeled along conductors 218 and 219 in the direction shown by arrows 350 (shown in FIGS. 2, 3, and 4).

Simultaneously, terahertz electromagnetic waves are received by terahertz insertion waveguide comprised of conductors 216 and 217 from antenna 109 (shown in FIG. 1) and the waves are channeled to the terahertz detection waveguide comprised of conductors 218 and 219, respectively, such that the waves can be transmitted across substrate member 212 and detected. When the terahertz electromagnetic waves are transmitted from terahertz insertion waveguide comprised of conductors 216 and 217 to the terahertz detection waveguide comprised of conductors 218 and 219, respectively, the waves come into contact with at least a portion the light pattern that is being directed onto the terahertz detection waveguide comprised of conductors 218 and 219 at junction portions 220 and 221, respectively. The terahertz electromagnetic waves move through the terahertz detection waveguide comprised of conductors 218 and 219 in the same direction as the illuminating light pattern along the terahertz detection waveguide comprised of conductors 218 and 219, as shown by arrows 350. The transmission of the waves and the illuminating light pattern within the terahertz detection waveguide comprised of conductors 218 and 219 facilitate the generation of a voltage, and the voltage forces at least one current through semiconductive pathway 250 and through waveguides 218 and 219. The current or analog signal representative of the current can be detected by amplifier 256, wherein the signal is converted to a digital output, processed with additional analog signal conditioning electronics (not shown), or displayed to the user via an analog meter (not shown).

In some embodiments, the terahertz insertion and detection waveguides 201 and 205, respectively, may also be constructed of three conductors (not shown) instead of two, in a ground-signal-ground architecture, also known as co-planar waveguide (CPW). The amplifier leads 252 would be connected to waveguide 205 with one lead (not shown) connected to, for example, a central conductor (not shown), and the other lead would be connected to the outer conductors (not shown). In such a configuration, there would be one area of semiconductor material (not shown) on each side of the central conductor, for a total of two. The light pattern would be directed at substrate 212 such that both areas of semiconductor would receive a portion of the light from the light pattern.

The digital output is transmitted to signal processing device 110 (shown in FIG. 1) via conduit 112 (shown in FIG. 1), wherein the digital output can be further analyzed. Signal processing device 110 can then generate a final output of the analysis. A signal representative of the final output can be transmitted from signal processing device 110 to display device 114 (shown in FIG. 1) such that the final output can be displayed to a user. The final output may include a graphical and/or a textual representation of, for example, the terahertz radiation that was transmitted through sample 106 (shown in FIG. 1). As such, the user is enabled to characterize sample 106. For example, by using the output representative of the detected terahertz waves (i.e., waves that move adjacent to sample 106 or are transmitted through some thickness of the sample material), the user can compare the detected waves with the overall terahertz radiation that was directed to sample 106. As such, the amount absorbed by sample 106 can be determined, which can facilitate ascertaining various characteristics of sample 106.

As compared to known systems that detect terahertz radiation, the above-described system includes a terahertz detection assembly that efficiently detects terahertz radiation. More specifically, the terahertz detection assembly includes a light generating apparatus that is configured to generate at least one illuminating light pattern that can be directed onto a substrate member having at least one waveguide and a semiconductive portion. As the illuminating light pattern is directed onto the substrate, the waveguide also receives a plurality of terahertz electromagnetic waves. The waves can be transmitted within the waveguide in the same direction as the motion of the illuminating pattern from the light generating apparatus. Such a technique facilitates the generation of a current that can be detected and further analyzed to facilitate the characterization of the terahertz electromagnetic waves that were received by the waveguide. The terahertz electromagnetic waves can be waves that have interacted with a sample that absorbs or reflects or transmits the waves as a function of the character of the sample, and/or the waves can be waves that passed next to the sample. The detection technique is relatively sensitive in detecting terahertz radiation. As such, a relatively large intensity wave source is not needed in, for example, evaluating the sample.

Exemplary embodiments of the assemblies, systems, and methods are described above in detail. The assemblies, systems, and methods are not limited to the specific embodiments described herein, but rather, components of the assemblies, systems, and/or steps of the method may be utilized independently and separately from other components and/or steps described herein. For example, the assembly may also be used in combination with other systems and methods, and is not limited to practice with only a system as described herein. Rather, the exemplary embodiment can be implemented and utilized in connection with many other systems.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A terahertz detection assembly comprising:
   a light generating apparatus configured to generate at least one illuminating light pattern; and
   a substrate member positioned proximate to said light generating apparatus, said substrate member comprising:
      a semiconductive portion configured to receive at least a portion of the at least one illuminating light pattern such that the received portion of the at least one illuminating light pattern is directed onto said semiconductive portion in a perpendicular direction with respect to said semiconductive portion to enable a conductive path to be defined within said semiconductive portion;
      a first waveguide coupled to said semiconductive portion such that said first waveguide is adjacent to the conductive path, said first waveguide is configured to receive a plurality of terahertz electromagnetic waves simultaneously with at least a portion of the at least one illuminating light pattern such that the at least one illuminating light pattern is moving along said first waveguide, said first waveguide comprises at least one first conductor that is configured to receive the plurality of terahertz electromagnetic waves that are transmitted within said first waveguide; and
      a second waveguide positioned adjacent to said first waveguide, wherein said second waveguide comprises at least one second conductor that is configured to facilitate channeling the plurality of terahertz electromagnetic waves in the same direction as the motion of the at least one illuminating light pattern from said light generating apparatus to facilitate the detection and characterization of the plurality of terahertz electromagnetic waves.

2. A terahertz detection assembly in accordance with claim 1, wherein the plurality of terahertz electromagnetic waves being transmitted within said first waveguide and the least one illuminating light pattern facilitate the generation of a voltage that channels at least one current through said first waveguide.

3. A terahertz detection assembly in accordance with claim 2, further comprising an amplifier coupled to said second waveguide, wherein said amplifier is configured to receive the at least one current from said second waveguide.

4. A terahertz detection assembly in accordance with claim 3, further comprising an analog-to-digital converter coupled to said amplifier.

5. A terahertz detection assembly in accordance with claim 1, wherein the at least one first conductor includes two first conductors and the at least one second conductor includes two second conductors.

6. A terahertz detection assembly in accordance with claim 1, wherein said substrate member further comprises at least one junction portion between said first waveguide and said second waveguide, wherein the at least one illuminating light pattern is in contact with the plurality of terahertz electromagnetic waves at said at least one junction portion.

7. A terahertz detection assembly in accordance with claim 1, wherein said light generating apparatus is configured to generate at least one moving spot of light from at least one pulsed light beam.

8. A terahertz detection assembly in accordance with claim 1, wherein said light generating apparatus is configured to generate a moving wave train of a plurality of propagating light beams.

9. A method of detecting terahertz radiation, said method comprising:
   positioning a substrate member proximate to a light generating apparatus, wherein the substrate member includes a semiconductive portion and a first waveguide that is coupled to the semiconductive portion and a second waveguide that is positioned adjacent to the first waveguide, wherein the first waveguide includes at least one first conductor and the second waveguide includes at least one second conductor;
   generating at least one illuminating light pattern by the light generating apparatus;
   directing at least a portion of the at least one illuminating light pattern onto the semiconductive portion in a perpendicular direction with respect to the semiconductive portion such that a conductive path is defined within the semiconductive portion;
   receiving a plurality of terahertz electromagnetic waves simultaneously with at least one illuminating light pattern via the first waveguide such that the at least one illuminating light pattern is moving along the first waveguide
   receiving the plurality of terahertz electromagnetic waves via the at least one first conductor of the first waveguide such that the plurality of terahertz electromagnetic waves are-channeled, via the at least one second conductor of the second waveguide, in the same direction as the motion of the at least one illuminating light pattern from the at least one illuminating light pattern to facilitate the detection and characterization of the plurality of terahertz electromagnetic waves.

10. A method in accordance with claim 9, further comprising:
generating a voltage; and
channeling at least one current, using the voltage, through the first waveguide.

11. A method in accordance with claim 10, further comprising transmitting the current to an amplifier that is coupled to the second waveguide.

12. A method in accordance with claim 9, wherein the at least one first conductor includes two first conductors and the at least one second conductor includes two second conductors.

13. A method in accordance with claim 9, further comprising contacting the at least one illuminating light pattern with the plurality of terahertz electromagnetic waves on at least one junction portion between the first waveguide and the second waveguide.

14. A method in accordance with claim 9, wherein generating at least one illuminating light pattern comprises generating at least one moving spot of light from at least one pulsed light beam.

15. A method in accordance with claim 9, wherein generating at least one illuminating light pattern comprises generating a moving wave train of a plurality of propagating light beams.

16. A system comprising:
an antenna; and
a terahertz detection assembly coupled to said antenna, said terahertz detection assembly comprising:
a light generating apparatus configured to generate at least one illuminating light pattern; and
a substrate member positioned proximate to said light generating apparatus, said substrate member comprising:
a semiconductive portion configured to receive at least a portion of the at least one illuminating light pattern such that the received portion of the at least one illuminating light pattern is directed onto said semiconductive portion in a perpendicular direction with respect to said semiconductive portion to enable a conductive path to be defined within said semiconductive portion;
a first waveguide coupled to said semiconductive portion such that said first waveguide is adjacent to the conductive path, said first waveguide is configured to receive a plurality of terahertz electromagnetic waves simultaneously with at least a portion of the at least one illuminating light pattern such that the at least one illuminating light pattern is moving along said first waveguide, said first waveguide comprises at least one first conductor that is configured to receive the plurality of terahertz electromagnetic waves that are transmitted within said first waveguide; and
a second waveguide positioned adjacent to said first waveguide, wherein said second waveguide comprises at least one second conductor that is configured to facilitate channeling the plurality of terahertz electromagnetic waves in the same direction as the motion of the at least one illuminating light pattern from said light generating apparatus to facilitate the detection and characterization of the plurality of terahertz electromagnetic waves.

17. A system in accordance with claim 16, wherein the plurality of terahertz electromagnetic waves being transmitted within said first waveguide and the least one illuminating light pattern facilitate the generation of a voltage that channels at least one current through said second waveguide.

18. A system in accordance with claim 17, wherein said terahertz detection assembly further comprises an amplifier coupled to said second waveguide, wherein said amplifier is configured to receive the at least one current from said second waveguide.

19. A system in accordance with claim 16, wherein the at least one first conductor includes two first conductors and the at least one second conductor includes two second conductors.

20. A system in accordance with claim 16, wherein said substrate member further comprises at least one junction portion between said first waveguide and said second waveguide, wherein the at least one illuminating light pattern is in contact with the plurality of terahertz electromagnetic waves at said at least one junction portion.

21. A system in accordance with claim 16, wherein said light generating apparatus is configured to generate at least one moving spot of light from at least one pulsed light beam.

22. A system in accordance with claim 16, wherein said light generating apparatus is configured to generate a wave train of a plurality of propagating light beams.

* * * * *